United States Patent [19]
Papenfuhs et al.

[11] Patent Number: 6,001,831
[45] Date of Patent: Dec. 14, 1999

[54] PROCESS FOR PRODUCING QUINAZOLINE DERIVATIVES

[75] Inventors: Theodor Papenfuhs, Frankfurt; Ralf Pfirmann, Griesheim; Stefan Krause; Doris Neumann-Grimm, both of Frankfurt, all of Germany

[73] Assignee: Clariant GmbH, Frankfurt, Germany

[21] Appl. No.: 09/029,723

[22] PCT Filed: Aug. 19, 1996

[86] PCT No.: PCT/EP96/03632

§ 371 Date: May 22, 1998

§ 102(e) Date: May 22, 1998

[87] PCT Pub. No.: WO97/08154

PCT Pub. Date: Mar. 6, 1997

[30]  Foreign Application Priority Data

Aug. 31, 1995 [DE] Germany .......................... 195 32 052

[51] Int. Cl.$^6$ .......................... A01N 43/66; C07D 241/36
[52] U.S. Cl. .......................... 514/249; 544/349
[58] Field of Search .......................... 514/249; 544/349

[56]  References Cited

FOREIGN PATENT DOCUMENTS

| 0176333 | 4/1986 | European Pat. Off. . |
|---|---|---|
| 0218999 | 4/1987 | European Pat. Off. . |
| 142507 | 6/1903 | Germany . |
| 19532054 | 3/1997 | Germany . |

OTHER PUBLICATIONS

Derwent Abstract—DE 19532054 A1—German Patent issued Mar. 6, 1997.
J. Am. Chem. Soc. (1933), pp. 2113–2116, "Quinazolines," by Lange & Sheibley.
Journal of the Chemical Society:(1948) Synthetic Antimalarials p. 1759–1766.
Süsse et. al., Monatsh Chem. (1987), vol. 118, pp. 71–79.

*Primary Examiner*—Mukund J. Shah
*Assistant Examiner*—Tamthom N. Truong
*Attorney, Agent, or Firm*—Scott E. Hanf

[57]  ABSTRACT

A process for producing 1,2,3,4-tetrahydro-2,4-dioxo-quinazoline-1-yl acetic acid derivatives of the formula (I) in which $R^1$, $R^2$, $R^3$ and $R^4$ are mutually independently hydrogen, halogen, OH, $NO_2$, ($C_1$–$C_6$) alkoxy, ($C_1$–$C_6$) alkyl, halogen-substituted ($C_1$–$C_6$) alkyl, $R^5$ is hydrogen, ($C_1$–$C_6$) alkyl, phenyl where the alkyl or phenyl radical may also be substituted by halogen atoms; in which an anthranilic acid derivative of formula (II), in which $R^1$ to $R^5$ have the above meaning and $R^6$ is hydrogen, ($C_1$–$C_6$) alkyl or phenyl, where the alkyl or phenyl radical may also be substituted by halogen atoms, is reacted with a metal cyanate and hydrogen chloride in the presence of an inert solvent.

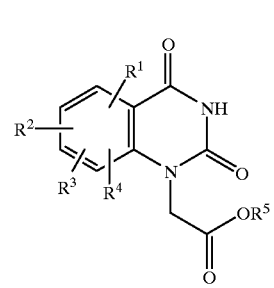

(I)

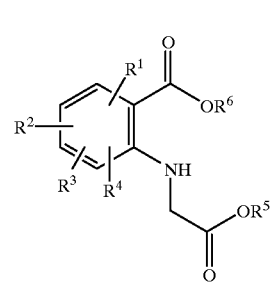

(II)

19 Claims, No Drawings

PROCESS FOR PRODUCING QUINAZOLINE DERIVATIVES

The present invention relates to a novel process for the preparation of 1,2,3,4-tetrahydro-2,4-dioxoquinazolin-1-ylacetic acid derivatives.

1,2,3,4-Tetrahydro-2,4-dioxoquinazolin-1-ylacetic acid and derivatives thereof are important intermediate products for the preparation of aldose reductase inhibitors (EP 218 999).

J. Am. Chem. Soc. (1933), pages 2113–2116 describes the reaction of N-ethylanthranilic acid with sodium cyanate and acetic acid and subsequent addition of sodium hydroxide to give 1,2,3,4-tetrahydro-1-ethyl-2,4-dioxoquinazoline. However, disadvantages of this process are the low space yield, because of the dilute reaction solution, and the very high excess of sodium hydroxide.

Monatsh. Chem. (1987) 118; pages 71–79 describes the reaction of methyl N-(methoxycarbonylmethyl)anthranilate with potassium cyanate in glacial acetic acid to give methyl 1,2,3,4-tetrahydro-2,4-dioxoquinazolin-1-ylacetate. Although 10 equivalents of potassium cyanate are employed, the yield is only 19%.

There was therefore the need for an efficient process for conversion of anthranilic acid into 1,2,3,4-tetrahydro-2,4-dioxoquinazolin-1-ylacetic acid derivatives.

This object is achieved by a process for the preparation of 1,2,3,4-tetrahydro-2,4-dioxoquinazolin-1-ylacetic acid derivatives of the formula (I)

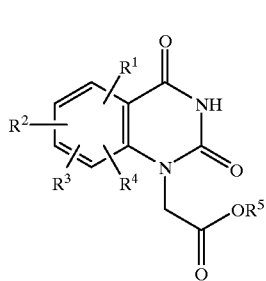

(I)

in which $R^1, R^2, R^3, R^4$ independently of one another are hydrogen, halogen, $NO_2$, $(C_1-C_6)$alkoxy, $(C_1-C_6)$alkyl or halogen-substituted $(C_1-C_6)$alkyl and $R^5$ is hydrogen, $(C_1-C_6)$alkyl or phenyl, where the alkyl or phenyl radical can also be substituted by halogen atoms, which comprises reacting an anthranilic acid derivative of the formula (II)

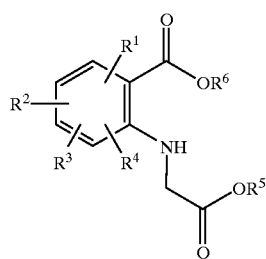

(II)

in which $R^1$ to $R^5$ have the abovementioned meaning and $R^6$ is hydrogen, $(C_1-C_6)$alkyl or phenyl, where the alkyl or phenyl radical can also be substituted by halogen atoms, with a metal cyanate and hydrogen chloride in the presence of an inert solvent.

The process is important for the reaction of compounds of the formula (II) in which $R^1$, $R^2$, $R^3$, $R^4$ are hydrogen, fluorine, chlorine, $(C_1-C_4)$alkoxy, $(C_1-C_4)$alkyl, or chlorine- or fluorine-substituted $(C_1-C_4)$alkyl and $R^5$ and $R^6$ are hydrogen, $(C_1-C_4)$alkyl or phenyl.

The reactions of compounds of the formula (II) in which $R^1$, $R^2$, $R^3$ and $R^4$ are hydrogen, fluorine, chlorine, methyl or ethyl,
and $R^5$ and $R^6$ are hydrogen, methyl or ethyl are important here.

The process is also particularly important for the preparation of compounds of the formula (I) in which two, and preferably three, of the radicals $R^1$, $R^2$, $R^3$ and $R^4$ are hydrogen.

The process is of particular interest for the preparation of 1,2,3,4-tetrahydro-7-chloro-2,4-dioxoquinazolin-1-ylacetic acid and the methyl and ethyl ester thereof.

In many cases, it has proved appropriate for the reaction to initially introduce the anthranilic acid derivatives of the formula (II) in a solvent. The anthranilic acid can be present here in dissolved form or as a suspension. Solvents which can be used are aprotic solvents or protic organic solvents or mixtures of these solvents. The use of polar aprotic solvents which show no reaction under the reaction conditions, for example sulfolane, dimethyl sulfoxide, dimethyl sulfone, diphenyl sulfone, tetramethylurea or mixtures thereof, is advantageous.

The concentration of anthranilic acid in the solvent is between 1 and 50% by weight, advantageously between 1.5 and 20% by weight, preferably between 3 and 10% by weight.

Metal cyanates which can be employed are alkali metal and alkaline earth metal cyanates, and also mixtures thereof. The use of sodium cyanate or potassium cyanate or mixtures thereof is advantageous.

It has proved favorable to add the metal cyanates in amounts of between 0.8 and 20 equivalents, in particular between 2 and 5 equivalents, based on the anthranilic acid derivatives. The metal cyanates can be initially introduced together with the anthranilic acid or added continuously or in portions. Hydrogen chloride can be added in gaseous form or as a non-aqueous solution, in one portion, in several portions or continuously, and continuous introduction of hydrogen chloride until the reaction has ended is advantageous.

The reaction partners metal cyanate, hydrogen chloride and anthranilic acid can be added to the reaction in any desired sequence, and it is advantageous to initially introduce the anthranilic acid and metal cyanate and to subsequently meter in the hydrogen chloride, or to initially introduce the hydrogen chloride and anthranilic acid and to subsequently meter in the metal cyanate, or to initially introduce the potassium cyanate and hydrogen chloride and to meter in the anthranilic acid, or to carry out combinations thereof.

The reaction temperature is between the solidification point of the solvent and 150° C., advantageously between 0 and 100° C., particularly advantageously between 20 and 75° C.

The reaction times are between 15 minutes and 24 hours, advantageously between 1 and 15 hours, particularly advantageously between 2 and 10 hours.

The reaction can be carried out under reduced, increased or normal pressure, and it is advantageously carried out under normal pressure.

The fact that the smooth course of the reaction is particularly surprising is demonstrated by the comparison example. It shows that the reaction can in no way be catalyzed generally by acids, but that the choice of the acid HCl is of decisive importance. The synthesis of the anthranilic acids of the formula (II) is described in the U.S. patent application Ser. No. 09/029,414, filed Apr. 4, 1998.

The following examples illustrate the invention without limiting it.

EXAMPLE 1

Preparation of ethyl 1,2,3,4-tetrahydro-7-chloro-2,4-dioxoquinazolin-1-ylacetate from 4-chloro-N-(ethoxycarbonylmethyl)anthranilic acid.

Hydrogen chloride is passed into 1 g of 4-chloro-N-(ethoxycarbonylmethyl)anthranilic acid and 1.6 g of potassium cyanate in 20 ml of sulfolane at 50° C. until analysis by HPLC indicates complete conversion. The product is precipitated by addition of water, filtered off, washed with water and dried. 0.95 g (87%) of ethyl 1,2,3,4-tetrahydro-7-chloro-2,4-dioxoquinazolin-1-ylacetate is obtained.

Melting point: 242–243° C., $^1$H NMR (DMF): 1.25 (t, J=7.0 Hz, —CH$_3$), 4.21 (q, J=7.0 Hz, O—CH$_2$—), 5.00 (s, N—CH$_2$), 7.38 (dd, J=1.8 Hz, J=8.2 Hz, 6-H), 7.70 (d, J=1.8 Hz, 8-H), 8.09 (d, J=8.2 Hz, 5-H), 11.86 (s, N—H).

EXAMPLE 2

Preparation of methyl 1,2,3,4-tetrahydro-7-chloro-2,4-dioxoquinazolin-1-ylacetate from methyl 4-chloro-N-(methoxycarbonylmethyl)-anthranilate.

Hydrogen chloride is passed into 1 g of methyl 4-chloro-N-(methoxycarbonylmethyl)anthranilate and 1.6 g of potassium cyanate in 20 ml of sulfolane at 50° C. until analysis by HPLC indicates complete conversion. The product is precipitated by addition of water, filtered off, washed with water and dried. 0.59 g (57%) of methyl 1,2,3,4-tetrahydro-7-chloro-2,4-dioxoquinazolin-1-ylacetate is obtained.

Melting point: 255–258° C. $^1$H-NMR (DMSO-d$_6$): 3.71 (s, —CH$_3$), 4.92 (s, N—CH$_2$), 7.33 (dd, J=1.5 Hz, J=8.5 Hz, 6-H), 7.60 (d, J=1.5 Hz, 8-H), 8.01 (d, J=8.5 Hz, 5-H).

EXAMPLE 3

Preparation of 1,2,3,4-tetrahydro-7-chloro-2,4-dioxoquinazolin-1-ylacetic acid from N-carboxymethylene-4-chloroanthranilic acid.

Hydrogen chloride is passed into a mixture of 20 ml of sulfone and 1.6 g of potassium cyanate at 25° C. to saturation. 1 g of N-carboxymethylene-4-chloroanthranilic acid is then added and the mixture is heated to 50° C. After three hours, analysis by HPLC indicates complete conversion into 1,2,3,4-tetrahydro-7-chloro-2,4-dioxoquinazolin-1-ylacetic acid.

Melting point: 278–282° C. $^1$H-NMR: (DMSO-d$_6$): 4.71 (s, N—CH$_2$), 7.30 (dd, J=1.5 Hz, J=8.5 Hz, 6H), 7.41 (d, J=1.5 Hz, 8-H), 7.99 (d, J=8.5 Hz, 5-H), 11.75 (s, N—H).

EXAMPLE 4

Preparation of ethyl 1,2,3,4-tetrahydro-7-chloro-2,4-dioxoquinazolin-1-ylacetate from 4-chloro-N-(ethoxycarbonylmethyl)anthranilic acid.

A total of 128 g of potassium cyanate and 144 g of hydrogen chloride are metered into 700 g of sulfolane at 15–20° C. over a period of 5 hours. For this, 14.4 g of hydrogen chloride are first passed in and 12.8 g of potassium cyanate are then added; this operation is repeated 10 times, until the entire amount of hydrogen chloride and potassium cyanate has been added. 117 g of 4-chloro-N-(ethoxycarbonylmethyl)anthranilic acid are then added at 45–50° C. in the course of 2 hours. The mixture is subsequently stirred for 15 minutes. The suspension is filtered and the residue is washed free from sulfolane and salt with water. After drying, 121 g (95%) of ethyl 1,2,3,4-tetrahydro-7-chloro-2,4-dioxoquinazolin-1-ylacetate are obtained.

EXAMPLE 5

Preparation of iso-propyl 1,2,3,4-tetrahydro-7-chloro-2,4-dioxoquinazolin-1-ylacetate from 7-chloro-N-(isopropoxycarbonylmethyl)anthranilic acid.

Hydrogen chloride is passed into a mixture of 10 g of sulfolane and 1.3 g of potassium cyanate at 20° C. to saturation. 1 g of 7-chloro-N-(isopropoxycarbonylmethyl)anthranilic acid is then added at 50° C. and the mixture is subsequently stirred for 30 minutes. The reaction mixture is poured onto water and filtered and the residue is washed with water and dried. 0.85 g (78%) of iso-propyl 1,2,3,4-tetrahydro-7-chloro-2,4-dioxoquinazolin-1-ylacetate is obtained.

$^1$H-NMR (DMSO-d$_6$): 1.21 (d, J=6.3 Hz, H$_3$C—C—CH$_3$), 4.88 (s, N—CH$_2$), 4.97 (sept, J=6.3 Hz, O—CH), 7.33 (dd, J=1.7 Hz, J=8.4 Hz, 6-H), 7.53 (d, J=1.7 Hz, 8-H), 8.00 (d, J=8.4 Hz, 5-H), 11.83 (s, N—H).

EXAMPLE 6

Preparation of n-hexyl 1,2,3,4tetrahydro-7-chloro-2,4dioxoquinazolin-1-ylacetate from 7-chloro-N-(n-hexoxycarbonylmethyl)anthranilic acid.

Procedure as under Example 5

Yield: 0.95 g (8%) $^1$H-NMR (DMSO-d$_6$): 0.84 (m, n-hexyl), 1.22 (m, n-hexyl), 1.55 (m, n-hexyl), 4.07 (m, n-hexyl), 4.92 (s, N—CH$_2$), 7.33 (dd, J=1.5 Hz, J=8.4 Hz, 6-H), 7.55 (d, J=1.5 Hz, 8-H), 8.01 (d, J=8.4 Hz, 5-H), 11.84 (s, N—H).

EXAMPLE 7

Preparation of benzyl 1,2,3,4tetrahydro-7-chloro-2,4-dioxoquinazolin-1-ylacetate from 7-chloro-N-(benzoxycarbonylmethyl)anthranilic acid.

Procedure as under Example 5.

Yield: 0.80 g (74%) $^1$H-NMR (DMSO-d$_6$): 5.01 (s, —CH$_2$—), 5.22 (s, —CH$_2$—), 7.36 (m, 6-H, aromatic-H), 7.59 (d, J=1.7 Hz, 8-H), 8.01 (d, J=8.4 Hz, 5-H), 11.86 (s, N—H).

EXAMPLE 8

Preparation of ethyl 1,2,3,4tetrahydro-5-fluoro-2,4-dioxoquinazolin-1-ylacetate from 6-fluoro-N-(ethoxycarbonylmethyl)anthranilic acid.

Procedure as under Example 5.

Yield: 0.60 g (54%). $^1$H-NMR (DMSO-d$_6$): 1.21 (t, J=7.1 Hz, —CH$_3$), 4.16 (q, J=7.1 Hz, —O—CH$_2$), 4.89 (s, N—CH$_2$), 7.06 (dd, J=8.5 Hz, J=11.0 Hz, aromatic-H), 7.14 (d, J=18.6 Hz, aromatic-H), 7.70 (dd, J=5.8 Hz, J=8.5 Hz, aromatic-H), 11.71 (s, N—H).

EXAMPLE 9

Preparation of ethyl 1,2,3,4-tetrahydro-8-chloro-2,4-dioxoquinazolin-1-ylacetate from 3-chloro-N-(ethoxycarbonylmethyl)anthranilic acid.

Procedure as under Example 5.

Yield: 0.70 g (64%). $^1$H-NMR (DMSO-d$_6$): 1.21 (t, J=7.1 Hz, —CH$_3$), 4.19 (q, J=7.1 Hz, —O—CH$_2$), 5.04 (s, N—CH$_2$), 7.30 (dd, J$_1$=J$_2$=7.8 Hz, aromatic -H), 7.81 (dd, J=1.7 Hz, J=7.8 Hz, aromatic-H), 8.04 (dd, J=1.7 Hz, J=7.8 Hz, aromatic-H), 11.97 (s, N—H).

EXAMPLE 10

Preparation of ethyl 1,2,3,4-tetrahydro-6-nitro-2,4-dioxoquinazolin-1-ylacetate from 5-nitro-N-(ethoxycarbonylmethyl)anthranilic acid.

Procedure as under Example 5.

$^1$H-NMR (DMSO-$d_6$): 1.22 (t, J=1.22 Hz, —CH$_3$), 4.18 (q, J=7.1 Hz, O—CH$_2$), 4.98 (s, N—CH$_2$), 12.19 (s, N—H).

COMPARISON EXAMPLE 1

1 ml of concentrated sulfuric acid is added dropwise to 1 g of 4-chloro-N-(ethoxycarbonylmethyl)anthranilic acid and 1.6 g of potassium cyanate in 20 ml of sulfolane at 50° C. After 5 hours, analysis by HPLC indicates no conversion.

COMPARISON EXAMPLE 2

2.4 g of acetic acid are added to 1 g of 4-chloro-N-(ethoxycarbonylmethyl)anthranilic acid and 1.6 g of potassium cyanate in 20 ml of sulfolane and the mixture is stirred at 50° C. After a reaction time of 6 hours, analysis by HPLC indicates a conversion of about 5%.

We claim:

1. A process for the preparation of a 1,2,3,4-tetrahydro-2,4-dioxo-quinazolin-1-ylacetic acid derivative of the formula (I)

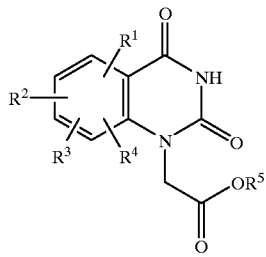

in which

R$^1$, R$^2$, R$^3$, R$^4$ independently of one another are hydrogen, halogen, NO$_2$, (C$_1$–C$_6$)alkoxy, (C$_1$–C$_6$)alkyl or halogen-substituted (C$_1$–C$_6$)alkyl and R$^5$ is hydrogen, (C$_1$–C$_6$)alkyl or phenyl, where the alkyl or phenyl radical can also be substituted by halogen atoms, which comprises reacting an anthranilic acid derivative of the formula (II)

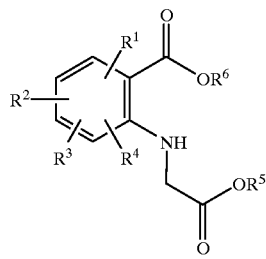

in which

R$^1$ to R$^5$ have the abovementioned meaning and R$^6$ is hydrogen, (C$_1$–C$_6$)alkyl or phenyl, where the alkyl or phenyl radical can also be substituted by halogen atoms, with a metal cyanate and hydrogen chloride in the presence of an inert solvent.

2. The process as claimed in claim 1, wherein R$^1$, R$^2$, R$^3$ and R$^4$ independently of one another are hydrogen, fluorine, chlorine, (C$_1$–C$_4$)alkoxy, (C$_1$–C$_4$)alkyl or chlorine- or fluorine-substituted (C$_1$–C$_4$)alkyl and R$^5$ and R$^6$ are hydrogen, (C$_1$–C$_4$)alkyl or phenyl.

3. The process as claimed in claim 1, wherein

R$^1$, R$^2$, R$^3$ and R$^4$ independently of one another are hydrogen, fluorine, chlorine, methyl or ethyl and R$^5$ and R$^6$ are hydrogen, methyl or ethyl.

4. The process as claimed in claim 1, wherein two of the radicals R$^1$, R$^2$, R$^3$ and R$^4$ are hydrogen.

5. The process as claimed in claim 1, wherein formula (I) is ethyl 1,2,3,4-tetrahydro-7-chloro-2,4-dioxoquinazolin-1-ylacetate, methyl 1,2,3,4-tetrahydro-7-chloro-2,4-dioxoquinazolin-1-ylacetate or 1,2,3,4-tetrahydro-7-chloro-2,4-dioxoquinazolin-1-ylacetic acid.

6. The process as claimed in claim 1, wherein a polar aprotic solvent is employed as the inert solvent.

7. The process as claimed in claim 1, wherein an alkali metal cyanate or alkaline earth metal cyanate is employed as the metal cyanate.

8. The process as claimed in claim 1, wherein the concentration of the anthranilic acid in the solvent is 1 to 50% by weight.

9. The process as claimed in claim 1, wherein the metal cyanate is added in an amount of 0.8 to 20 molar equivalents based on the anthranilic acid derivative.

10. The process as claimed in claim 1, wherein the hydrogen chloride is added in gaseous form or as a non-aqueous solution.

11. The process as claimed in claim 1, wherein the anthranilic acid derivative and the metal cyanate are initially introduced into the solvent and hydrogen chloride is metered in.

12. The process as claimed in claim 1 wherein the anthranilic acid derivative and hydrogen chloride are initially introduced and the metal cyanate is metered in.

13. The process as claimed in claim 1 wherein hydrogen chloride and the metal cyanate are initially introduced and the anthranilic acid derivative is metered in.

14. The process as claimed in claim 1, wherein the reaction temperature is between 0 and 100° C.

15. The process as claimed in claim 1, wherein the reaction time is between 15 minutes and 24 hours.

16. The process as claimed in claim 6, wherein said polar aprotic solvent is selected from the group of: sulfolane, dimethyl sulfoxide, dimethyl sulfone, diphenyl sulfone and tetramethylurea.

17. The process as claimed in claim 6, wherein said polar aprotic solvent is sulfolane.

18. The process as claimed in claim 7, wherein said alkali metal cyanate or alkaline earth metal cyanate is sodium cyanate or potassium cyanate.

19. The process as claimed in claim 1 wherein three of the radicals R$^1$, R$^2$, R$^3$ and R$^4$ are hydrogen.

* * * * *